United States Patent [19]
Janatpour et al.

[11] Patent Number: 4,697,034
[45] Date of Patent: Sep. 29, 1987

[54] PROCESS FOR MAKING DIARYL CARBONATES

[75] Inventors: Mojtaba Janatpour, Evansville, Ind.; Sheldon J. Shafer, Pittsfield, Mass.

[73] Assignee: General Electric Company, Pittsfield, Mass.

[21] Appl. No.: 815,205

[22] Filed: Dec. 31, 1985

Related U.S. Application Data

[63] Continuation-in-part of Ser. No. 551,718, Nov. 15, 1985, abandoned.

[51] Int. Cl.$^4$ ............................................. C07C 68/02
[52] U.S. Cl. ..................................................... 558/274
[58] Field of Search ........................................ 558/274

[56] References Cited

U.S. PATENT DOCUMENTS 2,335,441  11/1943  Pearson et al. ..................... 558/274
3,017,424   1/1982  Meyer et al. .
3,251,873   5/1966  Kurkjy et al. .
4,012,406   3/1977  Buysch et al. ..................... 558/274
4,016,190   4/1977  Bockmann et al. .

FOREIGN PATENT DOCUMENTS 1101386  12/1956  Fed. Rep. of Germany .
 841651   2/1958  United Kingdom .

Primary Examiner—Michael L. Shippen
Attorney, Agent, or Firm—Hedman, Gibson, Costigan & Hoare

[57] ABSTRACT

Diaryl carbonates, for example, diphenyl carbonate, are produced continuously by a two-step process wherein an alkali metal phenoxide compound is first produced from a phenolic compound and an alkali metal hydroxide, and thereafter the alkali metal phenoxide compound is reacted with an excess of phosgene at a temperature above the melting point of the diaryl carbonate product in a highly efficient reactor-mixer. Complete separation of the process steps and intimate admixing of the three-phase (gaseous, organic and aqueous) reaction mixture allows production of diaryl carbonates at high yield while avoiding excessive production of undesirable chloroformate intermediates.

11 Claims, 1 Drawing Figure

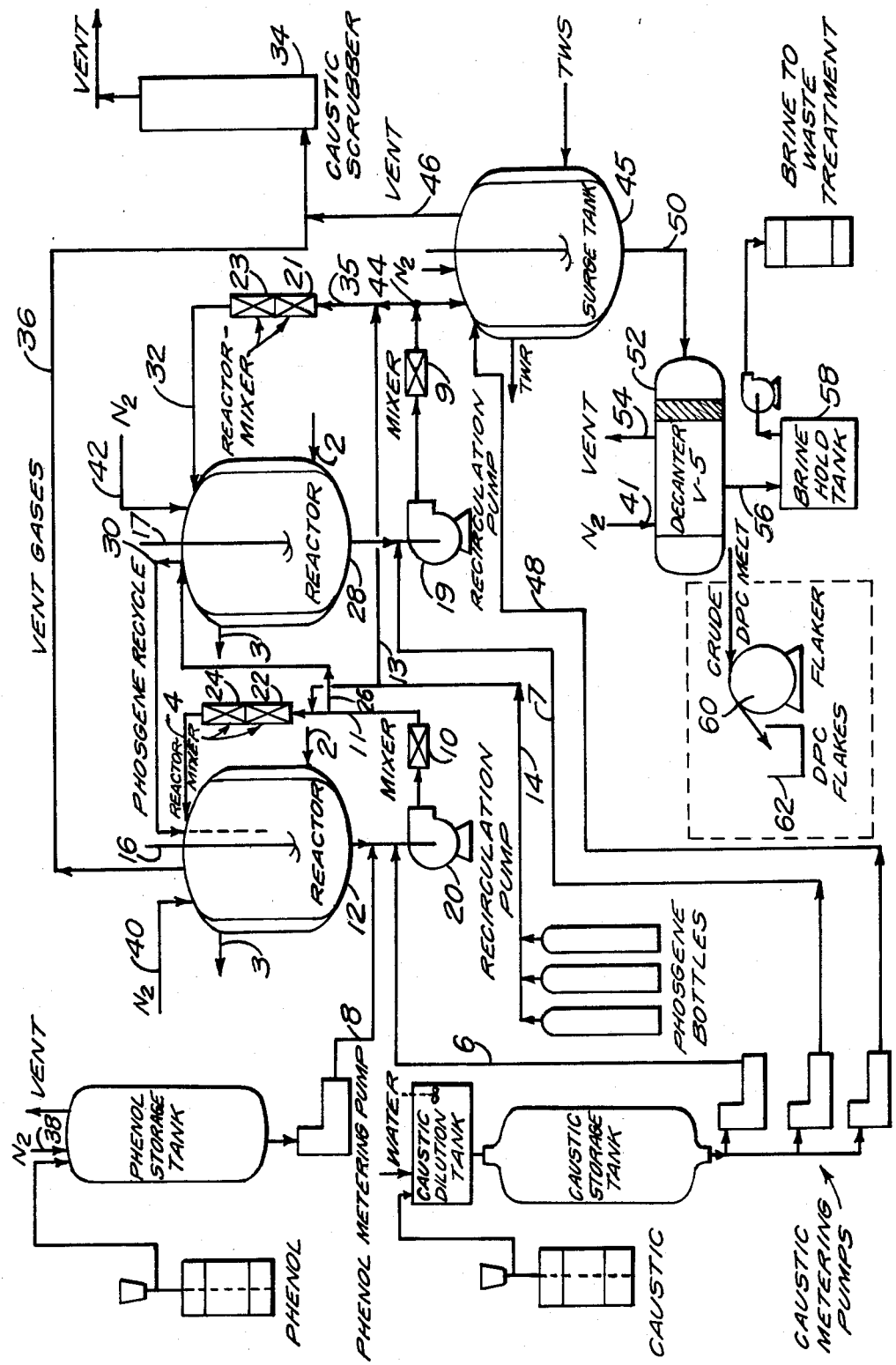

PROCESS FOR MAKING DIARYL CARBONATES

The present application is a continuation-in-part of copending U.S. patent application Ser. No. 551,718 filed Nov. 15, 1985, now abandoned.

BACKGROUND OF THE INVENTION

The present invention relates to the production of diaryl carbonates. More particularly, it relates to the continuous production of diaryl carbonates in the molten state using single and double recirculation loops.

The prior art processes for the production of diaryl carbonates include processes based on the use of armomatic hydroxy compounds reacted with phosgene in the presence of quaternary ammonium compounds or other tertiary amines as catalysts in the presence of water-immiscible solvents. It is also known to introduce phosgene into a highly alkaline solution of o-cresol at elevated temperatures to produce diarylcarbonates. See German Pat. Publication, OL No. 2509036, incorporated herein by reference.

Commercially, diaryl carbonates are made by a batch slurry process. Such a process is used to make diphenyl carbonates by reacting phosgene with phenol in the presence of caustic at a pH of 10-11, at 55°-60° C. The product is recovered as solid particles which are generally melted for hot water washing to remove the impurities. The major disadvantages of the process are the large volumes of water needed and solids handled and the poor quality of product due to the entrainment of phenyl chloroformate, salt and other impurities. The prior art batch processes have produced diaryl carbonates having phenylchlorocarbonic esters as byproduts and have yielded less than optimum yields of the desired product.

A leading use for diaryl carbonates is as reactants for making polycarbonates in transesterification reactions. If a diaryl carbonate such as diphenyl carbonate is contaminated with phenyl chloroformate, it will be difficult or impossible to produce a commercial grade of a polycarbonate molding resin.

Therefore, it is a principal object of this invention to provide a process for producing a diarylcarbonate in a highly pure form with high yields.

It is also an object of this invention to provide a process for making diaryl carbonates in high yields without requiring a catalyst.

It is also an object of this invention to provide a process for making diaryl carbonates which is operated continuously to produce diaryl carbonates in a highly pure form in high yields.

BRIEF DESCRIPTION OF THE DRAWINGS

The drawing is a flow diagram of an embodiment of the invention which shows continuous production of diphenyl carbonate in a double loop, although alternatively only one, or more than two loops, can be used.

DETAILED DESCRIPTION OF THE INVENTION

According to the present invention, a process for the synthesis of a diaryl carbonate comprises:
(a) contacting a phenolic compound with an alkali metal hydroxide in a first reaction zone to form an alkali metal phenolic compound;
(b) continuously contacting said alkali metal phenoxide with phosgene in a separate, second reaction zone at a temperature above the melting point of the diaryl carbonate being synthesized, preferably in a reactor-mixer producing a highly intimate admixture, wherein the initial three-phase reaction system (gaseous, aqueous, organic) passes rapidly through the chloroformate intermediate to yield the diaryl carbonate; and
(c) recovering substantially pure diaryl carbonate from said reaction mixture.

It is essential to carry out step (a) isolated from step (b), in order to avoid hydrolysis of the phosgene by the aqueous alkali metal hydroxide. The contacting of the phosgene with the two liquid phases (organic, comprising diaryl carbonate, phenolic compound, phenolic chloroformate; aqueous, comprising water, alkali metal chloride, alkali metal hydroxide, phenolic compounds and by-products), must also be carried out in a reactor-mixer producing a highly efficient mixing zone, for example a tubular motionless mixer. Under these conditions, very little chloroformate intermediate is entrained as an impurity and high yields of high purity diaryl carbonate are obtained.

The synthesis of the invention may also be carried out in the absence of a catalyst. This offers a significant advantage over prior art processes, which require the use of catalysts such as triethylamine. Eliminating the need for a catalyst simplifies the processing steps and reduces the material and training costs associated with large-scale production.

Synthesizing diaryl carbonates according to the process of this invention allows dramatically improved yields of around 90% or even higher to be obtained without specialized equipment or controls, as the working examples, infra, demonstrate.

The general scheme of the reactions occuring where the process of the invention is used to prepare diphenyl carbonate is as follows:

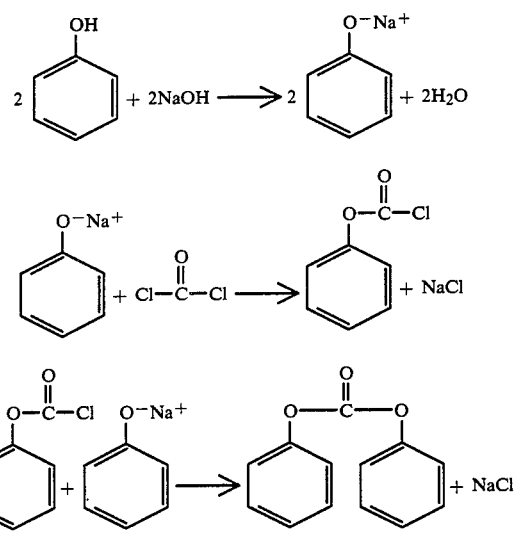

In addition to the use of highly efficient reactor-mixers for the phosgene reaction, the process of the invention is carried out so that the diaryl carbonate is produced in the molten state. For diphenyl carbonate, the melting point is 79° C. and thus it is convenient to utilize temperatures of from about 80°-88° C., although higher temperatures can be employed if desired.

The process is carried out in the molten state to avoid occluding any chloroformate, which is an undesirable contaminant in the diaryl carbonate product. The advantage of using the molten process is that it avoids the necessity of melting and washing the diaryl carbonate when this material is made in a suspension process.

In step (a) of the invention, alkali metal hydroxides such as lithium hydroxide, potassium hydroxide, sodium hydroxide or mixtures thereof may be utilized. Sodium hydroxide is preferred, and amounts of alkali metal hydroxide are utilized to maintain a pH level after phenoxide formation of from about 8.0 to above 9.1 or preferably from about 8.0 to about 8.3.

The alkali metal hydroxide and the phenolic compound are admixed and completely reacted in the absence of phosgene. This avoids hydrolysis of the phosgene by the aqueous alkali, which can be quite appreciable at the temperatures employed in the practice of the invention. The amount of alkali metal hydroxide utilized should be equimolar with the phenolic compound or less, so that substantially all of the alkali metal hydroxide is consumed in the reaction and converted to the phenoxide compound (and water). In practice, the reaction will be carried out in a separate zone or reaction vessel, for a period sufficient for the reaction mixture to reach the above desired pH of about 8.0 to 9.1. Preparing the alkali metal phenoxide compound in this way minimizes the amount of free alkali metal hydroxide in the later reaction stages, which, in turn, minimizes hydrolysis of the phosgene, as noted above. Thus, the process of the present invention conserves reagents and cuts down on the purification/recycling of undesirable by-products by utilizing less hydroxide than in prior art syntheses, conserving phosgene and avoiding excessive by-product salt and acid generation. Substantial elimination of the alkali metal hydroxide from the phosgenation step allows introduction of phosgene in more nearly stoichiometric amounts, thus minimizing the phosgene losses seen in prior art processes.

Most preferably, a mixture of about 80-90% of phenol in water as a feedstock and a solution of about 15-50% aqueous sodium hydroxice will be utilized for the preparation of sodium phenoxide in the synthesis of diphenyl carbonate.

The process of the invention is preferably applied to the synthesis of diphenyl carbonate using phenol as a reactant. Other symmetrical diaryl carbonates may be made using phenols such as 2-methylphenol; 3-methylphenol; 2,4-dimethylphenol; 2-methoxyphenol; 4-methoxyphenol; 2-chlorophenol and the like.

The process is preferably operated continuously in a suitable apparatus such as one of those to be described.

The product of the process is pure enough to be used in molten form directly in subsequent reactions, or it can be stored for later use. Optionally, it can be flaked or further purified.

The process is illustrated in the following examples, which are not intended to limit the scope of the claims in any manner.

DESCRIPTION OF THE PREFERRED EMBODIMENTS

EXAMPLES 1-15

A 5-neck, 500 ml, resin kettle equipped with a stirrer, phosgene inlet-sodium phenoxide delivery tube; nitrogen inlet-thermometer; pH electrode; and solution exit tube is used to make diphenyl carbonate. The sodium phenoxide is prepared in a mixing vessel where phenol in a phenol-water mixture is combined with a 45% by weight solution of sodium hydroxide. The sodium phenoxide is fed to a port in the loop and passed to a straight tube reactor-mixer. Gaseous phosgene is introduced immediately prior to the reactor-mixer. The exit conduit from the reactor-mixer is connected to the sodium phenoxide delivery tube and the solution exit tube. Fifteen runs were carried out starting with an initial charge of 250 ml of water and 188 g of phenol in the resin kettle. The sodium chloride (brine) and diphenyl carbonate phases were separated while molten without any further purification. The results are set forth in Table 1.

TABLE 1

PRODUCTION OF DIPHENYL CARBONATE

| Example | pH Range | Phosgene Flow Rate | Yield[1] Diphenyl Carbonate | Moles of Base Used | Phosgene Utilization | | |
|---|---|---|---|---|---|---|---|
| | | | | | Blown Out | Hydrolyzed | Diphenyl-Carbonate |
| 1 | 8.0-8.3 | 1 g/min | 194 g | 1.778 | 9% | 0% | 91% |
| 2 | 8.0-8.3 | 1 g/min | 194 g | 1.841 | 8% | 1% | 91% |
| 3 | 8.0-8.3 | 1 g/min | 195 g | 1.794 | 9% | 0% | 91% |
| 4 | 8.0-8.3 | 1 g/min | 198 g | 1.887 | 6% | 2% | 93% |
| 5 | 8.0-8.3 | 1 g/min | 190 g | 1.839 | 8% | 3% | 89% |
| 6 | 8.0-8.3 | (3) | 190 g | 1.806 | 9% | 2% | 89% |
| 7 | 8.0-8.3 | 1 g/min | 197 g | 1.806 | 8% | 0% | 92% |
| 8 | 8.0-8.3 | 1 g/min | 202 g | 2.048 | — | — | — |
| 9 | 8.0-8.3 | 1 g/min | 194 g | 1.839 | 8% | 1% | 91% |
| 10 | 8.0-8.3 | 1 g/min | 196 g | 1.952 | 2% | 6% | 92% |
| 11 | 8.5-8.7 | 1 g/min | 195 g | 1.919 | 4% | 5% | 91% |
| 12 | 8.5-8.7 | 1 g/min | 196 g | 1.871 | 6% | 2% | 92% |
| 13 | 8.9-9.1 | 1 g/min | 188 g | 2.000 | 0% | 12% | 88% |
| 14 | 9.3-9.5 | 1 g/min | Not Isolated | 3.016 | — | — | 10% |
| 15 | 8.0-8.3 | 1 g/min | 187 g | 1.825 | 9% | 4% | 87% |

| Example | % Phenol in Diphenyl Carbonate | % Phenol in Brine | Total Cl⁻ in Diphenyl carbonate (ppm) | Recirculation[2] Rate |
|---|---|---|---|---|
| 1 | 4.4 | 0.8 | 1246 | 180 ml/min |
| 2 | 3.7 | 0.8 | 532 | 180 ml/min |
| 3 | 5.0 | 1.0 | 415 | 180 ml/min |
| 4 | 3.0 | 0.7 | 510 | 180 ml/min |
| 5 | 5.7 | 0.8 | 487 | 180 ml/min |
| 6 | 6.0 | 0.9 | 523 | 180 ml/min |
| 7 | 2.5 | 1.1 | 780[7] | 180 ml/min |

TABLE 1-continued
PRODUCTION OF DIPHENYL CARBONATE

| | | | | |
|---|---|---|---|---|
| 8 | 2.8 | 0.6 | 349 | 180 ml/min |
| 9 | 7.0 | 0.8 | 1932 | 180 ml/min |
| 10 | 2.9 | 1.1 | 442 | 240 ml/min |
| 11 | 2.8 | 0.8 | 500 | 180 ml/min |
| 12 | 4.8 | 0.9 | 560 | 180 ml/min |
| 13 | 6.1 | 1.0 | 450 | 180 ml/min |
| 14 | — | — | — | 180 ml/min |
| 15 | 12.8 | 1.2 | 3100 | 120 ml/min |

(1)These values have been corrected for residual phenol.
(2)Recir. rates are relative; they have been calculated using hot water, not reaction mixture.
(3)½ phosgene added at 1 g/min, third quarter at 0.75 g/min and final quarter at 0.5 g/min.
(7)Toluene extract of crude diphenylcarbonate contained only 0.8 ppm chloride.

The results set forth in Table 1 demonstrate that the process of this invention is capable of producing diaryl carbonate with a high utilization of phosgene.

EXAMPLE 16

The process of the invention is carried out continuously in two loops an apparatus arranged according to the schematic drawing. The process comprises passing phenol through line 8 and sodium hydroxide through line 6 (caustic) to mixer 10 to form sodium phenoxide prior to encountering phosgene in reactor-mixers 22 and 24. The primary reactor vessels 12 and 28 are agitated to keep the two phases mixed. Recirculation pump 20 is used to feed the combined streams of lines 6 and 8 to mixer 10. Phosgene line 14 is connected to reactor-mixers 22 and 24 where it contacts the sodium phenoxide prior to being passed to the primary reactor vessel 12. Line 26 is connected to the outlet line 11 from mixer 10 and then to secondary reactor vessel 28 which is also provided with agitator 17, phosgene recycle line 30 and reaction loop 32, 35. Mixer 9 and reactor-mixers 21 and 23 perform functions the same as mixer 10 and reactor-mixers 22 and 24. Line 7 carries sodium hydroxide (caustic) to recirculation pump 19. Phosgene inlet 13 is connected to line 35 where it passes to reactor-mixers 21 and 23. Vent gases are passed to a caustic scrubber 34 through line 36. Nitrogen inlets 38, 40 and 42 provide an inert cover gas to primary reactor vessels and phenol storage tanks. A portion of the output of recirculation pump 19 is divided at coupling 44 and passed to surge tank 46 equipped with agitator 45 where gases are vented through line 46 and additional sodium hydroxide is added through line 48. Line 50 is used to pass crude diphenyl carbonate to decanter 52 which is provided with nitrogen inlet 41 and vent 54. The brine (NaCl) by-product from the reaction is withdrawn from the decanter through line 56 and passed to brine holding tank 58 prior to being pumped to a brine waste treatment facility. The diphenyl carbonate product can optionally be passed to flaker 60 which discharges flakes into receptacle 62.

Typically, the apparatus described in Example 16 is operated continuously by charging the primary reactor with 4 gallon of 95% phenol, maintained at a pH of 7.8-8.0 by 20% caustic and phosgenated at 12.5 pounds per hour while recirculating the reaction mixture through the loop prior to opening line 26. The pressure is maintained at 5 psig using a nitrogen blanket, and the temperature is kept at 71° C. by the flow of tempered water through water jacket inlet 2 and water jacket outlet 3. After addition of 70% phosgene for phenol conversion, a split stream is passed through line 26 to the secondary reactor maintaining a 40% level (9 gallons) in the primary reactor 12. At this time 95% phenol is fed through line 8 into the primary loop continuously at a 4 gallon per hour rate. Once the level of 9 gallons is established in the secondary reactor, the recirculation pump is started and phosgene is metered into the secondary reactor loop at the rate of 4.5 pounds per hour. The pH in the secondary reactor vessel 28 is maintained at 8.4. After levels are established in surge tank 46 and decanter 52, crude diphenyl carbonate is stored or optionally transferred to flaker 60 and brine is removed from the bottom.

In a series of trials the pH of secondary reactor 28 was varied from 8 to 8.8, and mixing and reaction residence time were varied. At lower pH, phenoxide concentration is decreased leading to lower conversion and higher undesirable phenylchloroformate conversion. At high pH excessive hydrolysis is encountered. Thus, the good operating pH for the secondary reactor is 8.2-8.6, preferably 8.4. Longer reaction residence time tends to decrease the amount of phenol in the crude product and increase overall phosgene utilization.

The phenol left in the crude diphenyl carbonate is typically 6-10% by weight.

Obviously, other modifications and variations of the present invention are possible in the light of the above teachings. For example, if o-cresol and o-chlorophenol, respectively, are substituted for phenol, di-ortho-cresyl carbonate and di-ortho-chlorophenyl carbonate will be produced. It is, therefore, to be understood that changes may be made in the particular embodiments of the invention described which are within the full intended scope of the appended claims.

We claim:
1. A process for the synthesis of a diaryl carbonate which comprises:
   (a) contacting a phenolic compound in a first reaction zone with an equimolar amount or less of an alkali metal hydroxide to form an alkali metal phenoxide compound,
   (b) reacting said alkali metal phenoxide compound with phosgene at a temperature above the melting point of the diaryl carbonate being synthesized in a second reaction zone comprising a reactor-mixer providing a highly intimate admixture of the initial reaction system to form the diaryl carbonate, and
   (c) recovering substantially pure diaryl carbonate from the reaction mixture;
wherein said steps (a) and (b) are carried out completely isolated from each other.

2. A process for the synthesis of a diaryl carbonate as defined in claim 1 wherein the diaryl carbonate is diphenyl carbonate.

3. A process for the synthesis of a diaryl carbonate as defined in claim 1 wherein the alkali metal hydroxide is sodium hydroxide.

4. A process for the synthesis of a diaryl carbonate as defined in claim 1 wherein the reaction is carried out as a continuous reaction.

5. A process for the synthesis of a diaryl carbonate as defined in claim 1 wherein the reaction is carried out in the absence of a catalyst.

6. A process for the continuous synthesis of a diphenyl carbonate which comprises:
(a) combining phenol and an alkali metal hydroxide to form an alkali metal phenoxide;
(b) passing said alkali metal phenoxide to a reactor-mixer provided with a phosgene supply, said reactor-mixer providing a highly efficient mixing zone and being at a temperature above the melting point of the diphenyl carbonate such that the three-phase reaction system which forms initially passes rapidly through a chloroformate intermediate to yield diphenyl carbonate;
(c) withdrawing said diphenyl carbonate from said reactor-mixer and separating said carbonate from the reaction by-products to obtain substantially pure diphenyl carbonate; wherein step (a) is carried out completely isolated from step (b).

7. A process for the continuous synthesis of diphenyl carbonate as defined in claim 6 wherein the alkali metal hydroxide is sodium hydroxide.

8. A process for the continuous synthesis of diphenyl carbonate as defined in claim 6 wherein the contents of the reactor-mixer are transferred to a second reactor-mixer provided with a phosgene supply and an alkali metal phenate supply prior to separation of the diphenyl carbonate from the reaction by-products.

9. A process for the continuous production of diphenyl carbonate as defined in claim 8 wherein the alkali metal phenoxide is contacted with phosgene at a temperature above the melting point of the diphenyl carbonate.

10. A process for the continuous production of diphenyl carbonate as defined in claim 8 wherein unreacted phosgene is recycled from the first to the second reactor-mixer.

11. A process for the production of diphenyl carbonate as defined in claim 8 wherein the process is carried out in the absence of a catalyst.

* * * * *